(12) United States Patent
Saint-Martin et al.

(10) Patent No.: US 6,537,509 B2
(45) Date of Patent: Mar. 25, 2003

(54) AUTOCLAVE STERILIZATION INSTALLATION

(75) Inventors: Bernard Saint-Martin, Montrouge (FR); Christiane Prioult, Lourdes (FR)

(73) Assignee: Isolateur Denominateur Commun, Lourdes (FR)

( * ) Notice: Subject to any disclaimer, the term of this patent is extended or adjusted under 35 U.S.C. 154(b) by 0 days.

(21) Appl. No.: 09/818,837

(22) Filed: Mar. 28, 2001

(65) Prior Publication Data

US 2002/0015672 A1 Feb. 7, 2002

(30) Foreign Application Priority Data

Mar. 29, 2000 (FR) .............................. 00 03967

(51) Int. Cl.⁷ ................................ A61L 2/00
(52) U.S. Cl. ..................... 422/297; 422/300; 422/307
(58) Field of Search ...................... 422/292, 294–297, 422/300, 305–308, 903, 905–907

(56) References Cited

U.S. PATENT DOCUMENTS

| 4,055,274 A | * 10/1977 | Waldenmeier et al. |
| 4,351,455 A | 9/1982 | Bond |
| 4,643,328 A | * 2/1987 | Lorenzelli et al. |
| 5,447,669 A | 9/1995 | Papciak et al. |
| 5,609,195 A | 3/1997 | Stricklin et al. |
| 5,853,207 A | * 12/1998 | Saint Martin et al. |

* cited by examiner

Primary Examiner—Robert J. Warden, Sr.
Assistant Examiner—Monzer R. Chorbaji
(74) Attorney, Agent, or Firm—Browdy and Neimark, P.L.L.C.

(57) ABSTRACT

An autoclave sterilization installation has a recovery outlet for recovering sterilized objects in such a way that the objects can be transferred in total safety. The recovery outlet is equipped with a removable rigid closure member which is adapted to withstand high pressures and includes an annular coupling flange which receives a recovery container which is preferably disposable. The closure member closes off the opening in the flange during the sterilization cycle.

9 Claims, 3 Drawing Sheets

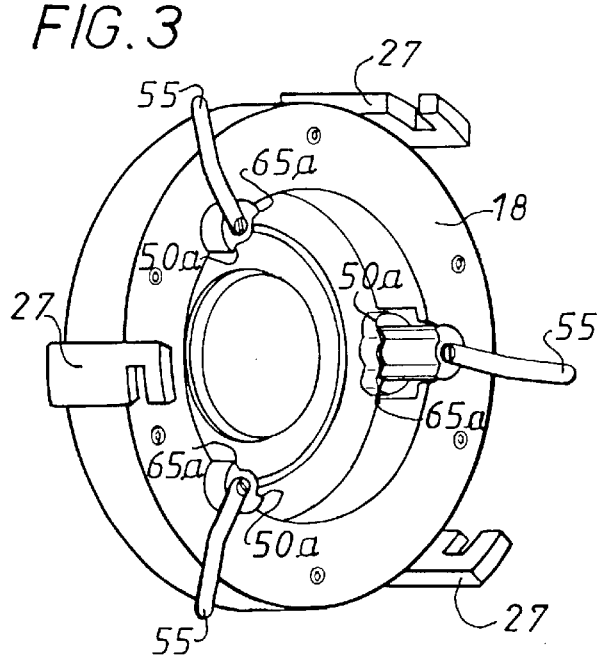
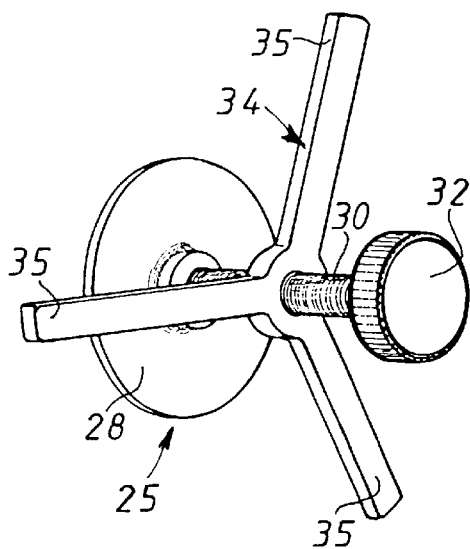
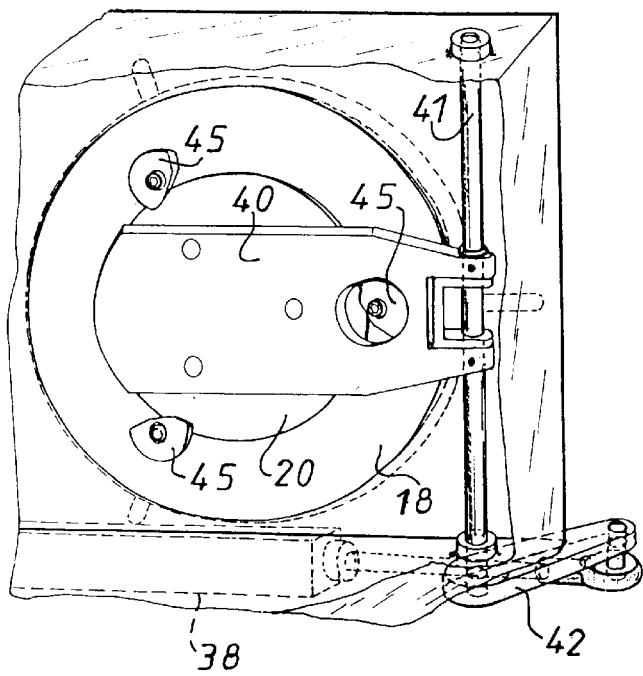

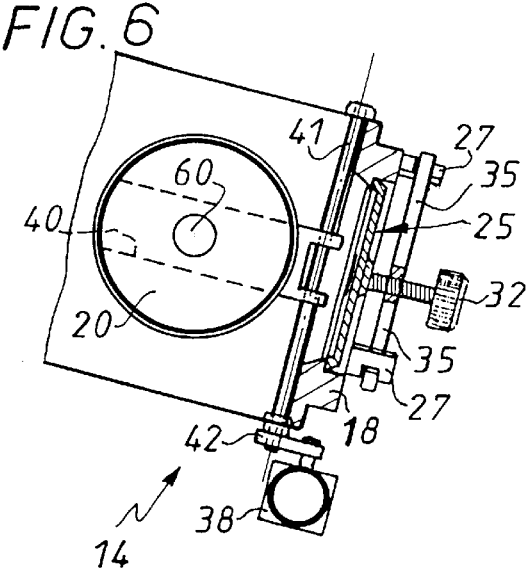
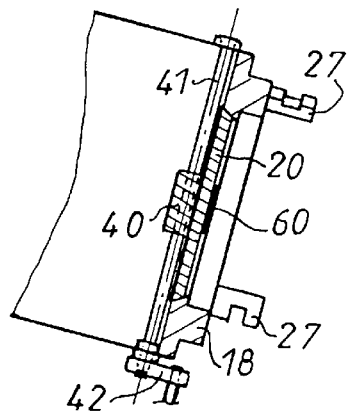
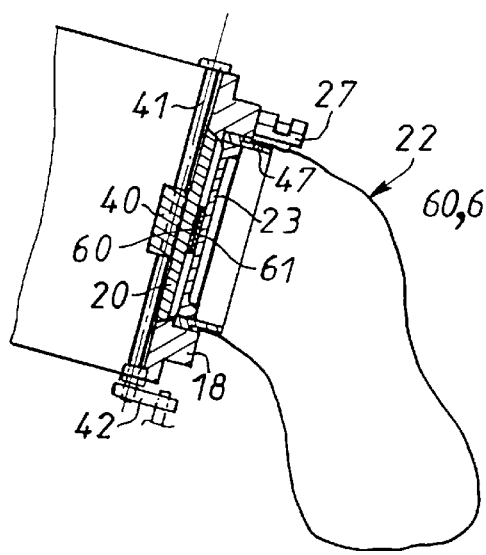
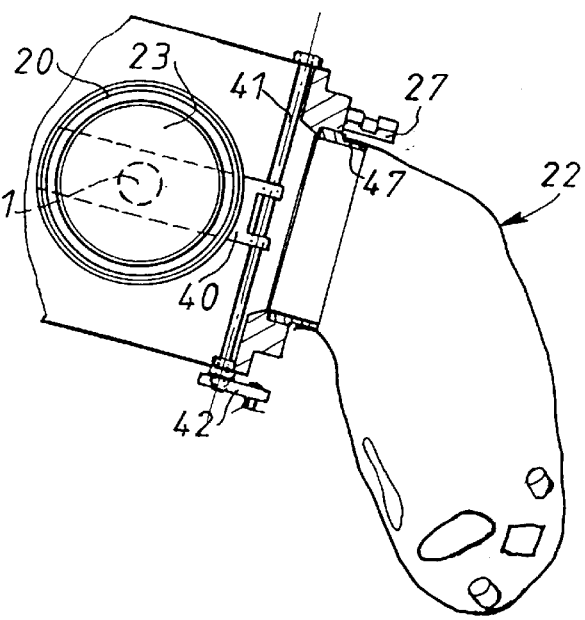
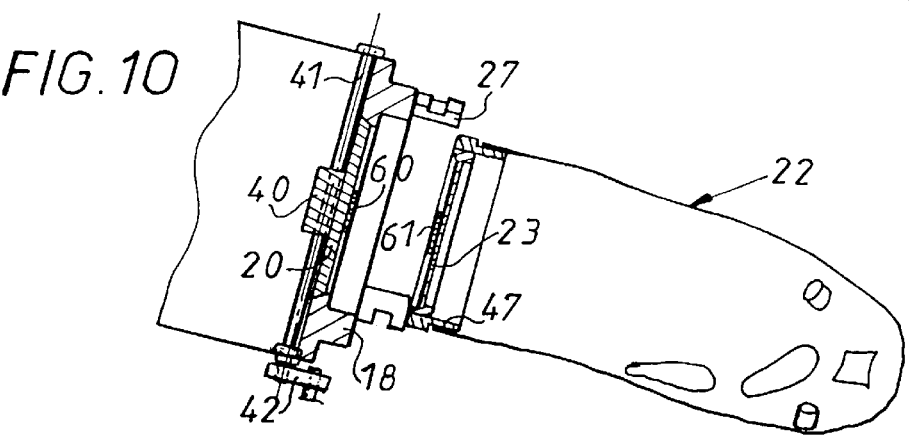

AUTOCLAVE STERILIZATION INSTALLATION

BACKGROUND OF THE INVENTION

1. Field of the Invention

The invention relates to an autoclave sterilization installation for sterilizing objects in which the autoclave has a recovery outlet for recovering sterilized objects.

The invention relates more particularly to an improvement to the recovery outlet.

2. Description of the Prior Art

In a conventional autoclave sterilization installation, the recovery outlet for sterilized objects is closed throughout the sterilization cycle. Like the rest of the autoclave, the door is designed to resist a temperature of the order of 140° C., an internal pressure of 3 to 5 bars and a vacuum of approximately 1 bar. Because the door is closed during sterilization, the inside face of the door is sterilized but not the outside face. Consequently, to recover sterilized objects with no risk of recontamination through contact with the outside environment, an isolator is fitted to the exterior of the housing of the autoclave, around the object recovery outlet, and a chemical sterilizing product is injected into the isolator at atmospheric pressure to sterilize the outside of the door before it is opened. The objects are then transferred into the isolator and placed in sealed and sterile containers by an operator wearing a captive glove.

This method of recovering sterilized objects is complicated and wastes time. It also necessitates an isolator, which constitutes a costly additional device necessitating the use of active sterilizing gas at atmospheric pressure.

A sealed connecting device between two enclosures isolated from an external environment and able to communicate with no contact with said external environment, even momentary contact, is known in the art. The principle of a device of this kind is described in French patent application N° 94.07430 filed Jun. 17, 1994, for example.

In principle this kind of device was developed for carrying out transfer operations at atmospheric pressure.

The basic idea of the invention is to use the above kind of device in combination with other elements used during the sterilization process to withstand the pressures referred to above, the combination eliminating the need for an isolator when sterilized objects are recovered.

SUMMARY OF THE INVENTION

The invention provides an autoclave sterilization installation for sterilizing objects, the installation including a sterilization housing with a recovery outlet for recovering sterilized objects, which recovery outlet is equipped with a removable rigid closure member adapted to withstand pressures employed during an operating cycle, a fixed annular coupling flange with an inwardly opening door, means for locking the closure member to the annular coupling flange to close off the recovery outlet during a sterilization cycle executed with the door open, means for pressing a rigid annular flange of a recovery container against the coupling flange, and a door shaped to fit face-to-face to the inwardly opening door.

The inwardly opening door is therefore left open during the sterilization cycle and it is the rigid closure member that withstands the high pressure or the vacuum during this period. At the end of the sterilization cycle, when the pressure inside the autoclave has returned to atmospheric pressure, the door is closed, the rigid closure member is demounted and a recovery container as referred to above, for example of the kind described in the French patent application referred to above, is fixed to the annular coupling flange.

In one embodiment the rigid closure member includes a clamping screw extended by an operating handle and a bracing member is screwed to the clamping screw. The bracing member has three arms which cooperate with hooks fixed along the perimeter of the annular coupling flange attached to the sterilized object recovery outlet.

The recovery container referred to above is advantageously disposable, as is known in the art and described in the patent application referred to above.

The invention will be better understood and its other advantages will become more clearly apparent in the light of the following description of an autoclave sterilization installation in accordance with the invention, which description is given by way of example only and with reference to the accompanying drawings.

BRIEF DESCRIPTION OF THE DRAWINGS

FIG. 3 shows a coupling flange of the recovery outlet.

FIG. 4 shows the same annular coupling flange fitted with the inwardly opening pivoted door, as seen from the inside.

FIG. 5 is a perspective view of a rigid closure member.

FIGS. 6 to 10 are diagrams showing successive phases of the process of sterilizing objects and recovering the treated objects.

DETAILED DESCRIPTION OF THE PREFERRED EMBODIMENT

Figure 1:
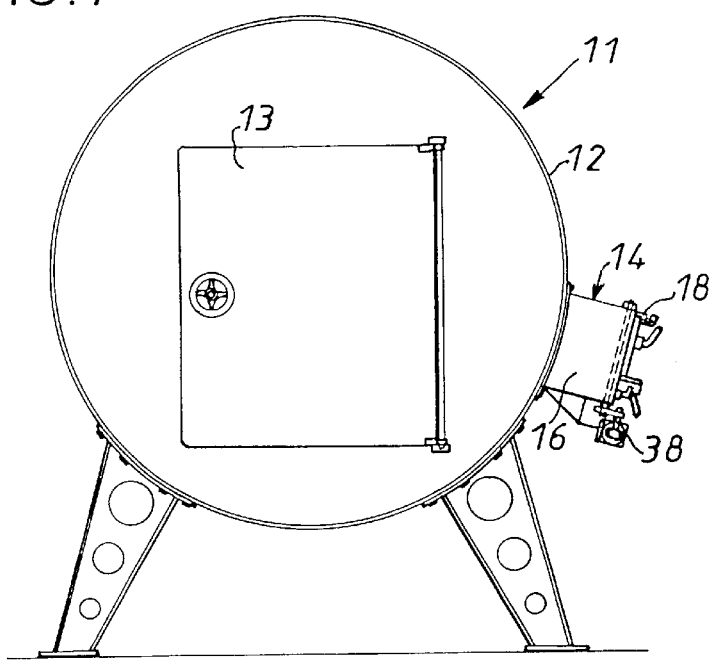
FIG. 1 is a diagrammatic elevation view of an autoclave sterilization installation in accordance with the invention.
Figure 2:
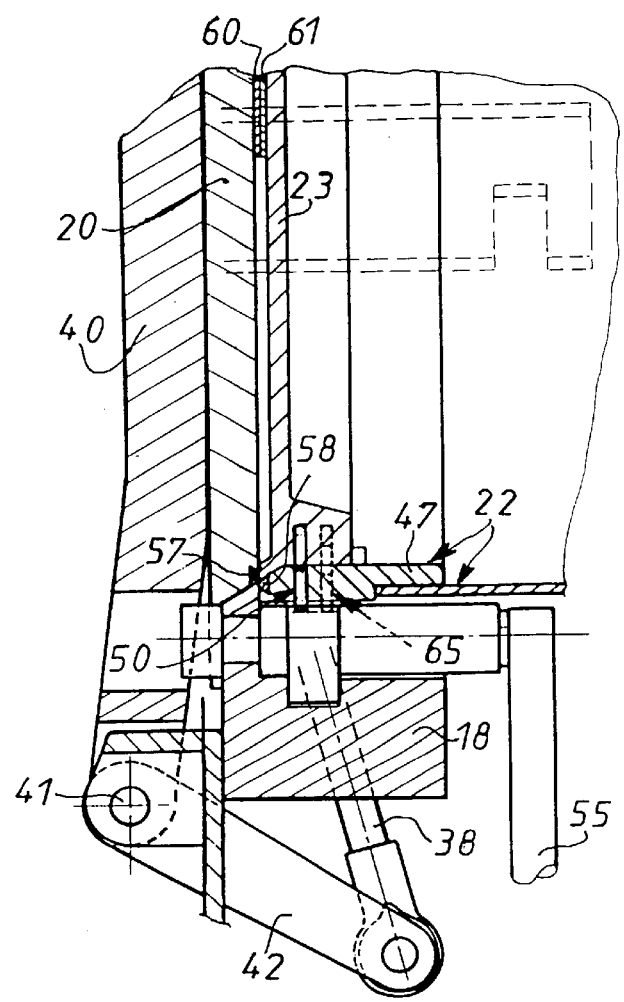
FIG. 2 is a sectional view to a larger scale of a sterilized object recovery outlet during a phase of connection to a disposable recovery container.

Referring to FIGS. 1 to 5 in particular, the autoclave sterilization installation 11 includes a sealed housing 12 which has a loading door 13 for inserting objects to be treated and a recovery outlet 14 for sterilized objects. The invention is more particularly concerned with the structure of the recovery outlet, which is at the end of a tubular section 16 attached to and projecting from the flank of the autoclave. The recovery outlet has a fixed annular coupling flange 18 fitted with a door 20 that opens by pivoting inwards. The essential function of the door is to enable safe transfer of sterilized objects to a disposable container 22 itself having a door 23 which can be coupled to the pivoting door 20 during transfer by a process that is described later. The pivoting door is not necessarily designed to withstand high pressures.

The sterilization installation is completed by a removal rigid closure member 25, seen in FIG. 5, adapted to withstand the pressures employed during the operating cycle of the autoclave. The recovery outlet 14 is equipped with locking means 27 for fixing the closure member to the annular coupling flange to close off the recovery outlet during a sterilization cycle performed with the door open.

The rigid closure member 25 therefore includes a circular plate 28 which closes off the opening in the flange 18 (see FIG. 6). A clamping screw 30 is attached to the center of the plate. To be more precise, the end of the screw terminates in a ball (not visible in FIG. 5) trapped in a cavity at the center of the plate. The other end of the clamping screw is attached to an operating handle 32 and a bracing member 34 with three arms 35 is screwed onto the clamping screw. The arms cooperate with hooks 36 fixed along the perimeter of the annular coupling flange 18 fastened to the sterilized object recovery outlet.

The door 20 which opens inwards, i.e. which pivots inside the section 16, is actuated by a controlled actuator 38. As can be seen in FIG. 4, the door 20 is fixed internally to a support 40 which is itself fastened to a rotatable shaft 41 one end of which projects out of the tubular section 16 near the recovery outlet. The actuator 38 is coupled to this end of the shaft by a link 42. Movement of the piston rod of the actuator therefore pivots the link and the shaft, which opens or closes the door 20. Closure is confirmed by three cams 45 fastened to external maneuvering handles provided at the edge of the flange.

The recovery outlet 14 for recovering sterilized objects is equipped with means for pressing a rigid annular flange 47 of a recovery container 22 against the coupling flange 18, similar to the means described in the previously mentioned French patent application N° 94.07430, for example. The recovery container is preferably disposable. The door 23 is shaped to fit face-to-face against the inwardly opening door 20 when the latter is in the position shown in FIG. 4.

In accordance with a feature that is known in the art but which is advantageous in the context of the invention, the disposable container used to recover the objects includes means 50 for finally locking its own door, controlled by first actuator means 50a installed in the vicinity of the recovery outlet. The first actuator means consist of cams moving inside the flange 18 and operated by handles 55. Mutual attachment and separation of the doors and the establishing of communication between the two enclosures are controlled in accordance with a procedure that avoids all risk of contact of the content of either enclosure with the outside environment. Thus the two doors are provided with cooperating mutual attachment means enabling them to be assembled one against the other in a hermetically sealed manner so that their outside faces are isolated from each other. The outlet door 20 of the autoclave is fitted with an annular elastomer seal 57 against which a projecting outside edge of the door 23 of the disposable container is pressed. The periphery of the latter door is equipped with an annular seal 58 which is pressed onto the edge of the flange in the immediate vicinity of the seal 57. Respective fastening members operating merely by mutual contact are attached to the outside faces of the two doors 20, 23. The members at the centers of the doors are magnetic plates 60, 61 or adhesive plates or other similar systems, for example. Each plate fixed to the center of one of the doors is adapted to attach itself to the other one.

The means for finally locking the disposable container consist of an arrangement with three holes at 120° through the disposable container flange, three corresponding blind holes in the thickness of the door of the container aligned with the holes in the flanges, and three pins or the like engaged in the hole in the flange 47. The length of the pins is greater than the thickness of the flange of the disposable container and the pins therefore project out of the container before it is used. The first actuator means 50a include three members with pivoting cams at 120° installed near the door of the recovery outlet and operated by the handles 55. The cams are shaped and located to cooperate with the pins.

The disposable container further includes means 65 for initially locking its own door which are adapted to be inhibited by second actuator means 65a attached to the outlet. The initial locking means include an arrangement with three holes passing through the flange 47 of the disposable container, three blind holes in the thickness of the door of the container aligned with the holes in the flange, and inside and outside pins or the like engaged one behind the other in each pair of aligned holes. Before use, each inner pin is engaged both in the flange 47 and in the door 23 and the internally sterile disposable container is therefore hermetically sealed. Each outer pin projects from the flange before use. The second actuator means 65a comprise three members with pivoting cams installed on the edge of the outlet 14 and shaped to cooperate with the corresponding outside pins. The lengths of the inside and outside pins are such that their ends in contact are located at the interface between the flange and the door when the second actuator means operate on the outside pin.

As shown in FIG. 3, the first and second actuator means are combined. Each member operated by a handle 55 includes two cams for actuating the pins.

To carry out a transfer, the door 23 of the container 22 is brought into contact with the outside face 20 of the pivoting door, which is closed by the actuator 38. The situation is then that shown in FIG. 2. A first action on the three handles 55 pushes in the pins of the initial locking means so that the door 23 is temporarily detached from the flange 47. It then remains attached to the pivoting door. When the disposable container has been filled, the pivoting door 20 is closed and the handles 55 are actuated in the opposite direction to press in the pins of the final locking means, which finally locks and hermetically seals the door 23 to the flange 47.

FIGS. 6 to 10 show phases of the sterilization process.

In FIG. 6, the objects previously inserted into the autoclave are being sterilized. During this phase the pivoting door 20 is left open inside the tubular section 16 and the closure member 25 is pressed firmly against the flange. Consequently, the pivoting door is sterilized on both sides.

In FIG. 7, the pivoting door 20 has been closed by means of the actuator and the closure member 34 has been removed.

In FIG. 8 a disposable container 22 to receive the sterilized object has been connected to the flange 18.

Initially, the outside faces of the two doors are brought into contact, which isolates them from each other. The initial locking means are released by pressing in the pins and the pivoting door coupled to the door of the disposable container is opened by the actuator. The sterilized objects are then transferred into the disposable container 22 (FIG. 9).

The door 20 is closed by operating the actuator and the final locking means are actuated. The disposable container 22 can then be detached from the recovery outlet 14 (FIG. 10) and the objects that it contains can be transferred in the container to a place of storage or use.

What is claimed is:

1. An autoclave sterilization installation for sterilizing objects, said installation comprising:

a sterilization housing having a recovery outlet for recovering sterilized objects, said recovery outlet being provided with a fixed annular coupling flange with an inwardly opening door, a removable rigid closure member adapted to withstand pressures employed during an operating cycle of said installation and means for locking said removable rigid closure member to said fixed annular coupling flange to close off said recovery outlet during a sterilization cycle executed with said door open, and means for pressing a rigid annular flange of a recovery container against said fixed annular coupling flange when said removable rigid closure member is removed from said fixed annular coupling flange.

2. The installation claimed in claim 1 wherein said inwardly opening door is actuated by a controlled actuator.

3. The installation claimed in claim 1 wherein said rigid closure member includes: a clamping screw extended by an operating handle; and a bracing member screwed to said clamping screw and cooperating with hooks fixed along the perimeter of said fixed annular coupling flange.

4. The installation claimed in claim 1 wherein said recovery container is disposable.

5. The installation claimed in claim 4 wherein said disposable container includes final locking means for its own door actuated by first actuator means installed in the vicinity of said recovery outlet.

6. The installation claimed in claim 5 wherein said final locking means of said disposable container include an arrangement comprising a hole through said flange of said disposable container, a blind hole in the thickness of said door of said container aligned with said hole in said flange, and a pin or the like engaged in said hole in said flange, and wherein the length of said pins is greater than the thickness of said flange, said pins projects out of said flange before said container is used and said first actuator means include a member with pivoting cams installed near the edge of said recovery outlet and shaped and located to cooperate with said pins.

7. The installation claimed in claim 6 wherein said disposable container further includes initial locking means for its own door adapted to be inhibited by second actuator means attached to said recovery outlet.

8. The installation claimed in claim 7 wherein said initial locking means include an arrangement comprising a hole through said flange of said disposable container, a blind hole in the thickness of said door of said container aligned with said hole in said flange, and inside and outside pins or the like engage one behind the other in said two holes, said inside pin is engaged both in said flange and in said door and said outside pin then projecting out of said flange before said container is used, said second actuator means include a member with pivoting cams installed at the edge of said recovery outlet and shaped to cooperate with said outside pins, and the length of said pins is such that their ends in contact are located at the interface between said flange and said door when said second actuator means are operating on said outside pin.

9. The installation claimed in claim 6 wherein said initial locking means include an arrangement comprising a hole through said flange of said disposable container, a blind hole in the thickness of said door of said container aligned with said hole in said flange, and inside and outside pins or the like engage one behind the other in said two holes, said inside pins are engaged both in said flange and in said door, said outside pins project out of said flange before said container is used, said second actuator means include a member with pivoting cams installed at the edge of said recovery outlet and shaped to cooperate with said outside pins, the length of said pins is such that their ends in contact are located at the interface between said flange and said door when said second actuator means are operating on said outside pins, and said first and second actuator means are combined.

* * * * *